(12) United States Patent
Sevenster

(10) Patent No.: US 8,935,287 B2
(45) Date of Patent: Jan. 13, 2015

(54) SYSTEM AND METHOD FOR STORING A CANDIDATE REPORT

(75) Inventor: Merlijn Sevenster, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 341 days.

(21) Appl. No.: 13/264,541

(22) PCT Filed: Apr. 15, 2010

(86) PCT No.: PCT/IB2010/051645
§ 371 (c)(1),
(2), (4) Date: Oct. 14, 2011

(87) PCT Pub. No.: WO2010/119421
PCT Pub. Date: Oct. 21, 2010

(65) Prior Publication Data
US 2012/0036160 A1  Feb. 9, 2012

(30) Foreign Application Priority Data
Apr. 17, 2009 (EP) .................................... 09158142

(51) Int. Cl.
G06F 17/30 (2006.01)
G06F 19/00 (2011.01)

(52) U.S. Cl.
CPC .................................. *G06F 19/3487* (2013.01)
USPC ........... 707/780; 707/740; 707/737; 707/736; 707/E17.014; 715/230; 715/231; 715/268; 705/2; 705/3; 600/407; 600/437; 382/132; 382/128

(58) Field of Classification Search
CPC ....... G06F 19/3487; G06F 7/60; G06F 17/30; G06F 17/24; G06F 1/24; G06F 17/306; G06F 17/3011; G06F 19/321; G06F 19/322; G06Q 50/00; G06Q 50/22; H04N 7/025

USPC .......... 707/780, 740, 758, E17.089, E17.061, 707/E17.014, 737, 736, 752, E17.027, 707/E17.026, E17.031, E17.02; 382/128, 382/132; 600/407, 437, 443, 451, 465, 468; 715/233, 230, 231, 268; 705/2, 3
See application file for complete search history.

(56) References Cited

U.S. PATENT DOCUMENTS 7,216,110 B1 * 5/2007 Ogg et al. ........................ 705/80
7,222,130 B1   5/2007 Cras et al.
(Continued)

OTHER PUBLICATIONS

Srinivasan Parthasarathy and Rajiv Gandhi—"Distributed Algorithms for Coloring and Domination in Wireless Ad Hoc Networks"—FSTTCS 2004: Foundations of Software Technology and Theoretical Computer Science—Computer Science vol. 3328, 2005, pp. 447-459.*

(Continued)

*Primary Examiner* — Anh Ly

(57) ABSTRACT

Extensive databases of well-annotated reports are important knowledge sources in medical workflows, such as in radiology. These are typically accessed by the healthcare professional looking for reports similar to a current case being evaluated. However, filling and maintaining such databases requires considerable effort. A system is provided for storing a candidate report, comprising a searcher configured to retrieve one or more queries from a query database; to retrieve the candidate report from a user input; to execute the one or more queries on the candidate report to determine the relevance of the candidate report, and to store the candidate report in the report database if the relevance exceeds a predetermined value. This provides a check, prior to storing, to evaluate whether a candidate report would actually be a worthwhile addition to the database. If not, it is by default not added.

19 Claims, 3 Drawing Sheets

(56) References Cited

U.S. PATENT DOCUMENTS

| | | | |
|---|---|---|---|
| 7,496,567 B1* | 2/2009 | Steichen | 707/999.003 |
| 7,957,568 B2* | 6/2011 | Adachi et al. | 382/128 |
| 2003/0005464 A1* | 1/2003 | Gropper et al. | 725/115 |
| 2004/0243545 A1* | 12/2004 | Boone et al. | 707/2 |
| 2005/0060199 A1 | 3/2005 | Siegel | |
| 2005/0075544 A1* | 4/2005 | Shapiro et al. | 600/300 |
| 2005/0135662 A1* | 6/2005 | Vining et al. | 382/128 |
| 2005/0192143 A1* | 9/2005 | Sasaki et al. | 474/101 |
| 2005/0273810 A1* | 12/2005 | Zimmerman et al. | 725/34 |
| 2006/0177114 A1* | 8/2006 | Tongdee et al. | 382/128 |
| 2006/0224581 A1* | 10/2006 | Sasai | 707/5 |
| 2006/0253423 A1* | 11/2006 | McLane et al. | 707/2 |
| 2007/0053567 A1* | 3/2007 | Adachi et al. | 382/128 |
| 2007/0083396 A1* | 4/2007 | Kanada et al. | 705/3 |
| 2007/0192134 A1* | 8/2007 | Littenberg et al. | 705/2 |
| 2008/0126131 A1* | 5/2008 | Lou | 705/3 |
| 2008/0141107 A1* | 6/2008 | Catallo et al. | 715/201 |
| 2008/0288451 A1* | 11/2008 | Jiang et al. | 707/3 |
| 2008/0300917 A1* | 12/2008 | Ryan et al. | 705/2 |
| 2009/0083074 A1* | 3/2009 | Shioe | 705/3 |
| 2010/0076780 A1* | 3/2010 | Mahesh et al. | 705/2 |
| 2010/0145720 A1* | 6/2010 | Reiner | 705/2 |
| 2011/0110568 A1* | 5/2011 | Vesper et al. | 382/128 |
| 2011/0135174 A1* | 6/2011 | Vining et al. | 382/128 |
| 2011/0276346 A1* | 11/2011 | Reiner | 705/3 |
| 2012/0330876 A1* | 12/2012 | Bryce | 706/47 |

OTHER PUBLICATIONS

Asada, Y. ; Kanno, T. ; and Furuta, K.—"Application of Semantic Web to Incident Reporting"—Published in: SICE-ICASE, 2006. International Joint Conference—Date of Conference: Oct. 18-21, 2006—pp. 955-958.*

By Ramasawamy et al, MoSearch: A Radiologist Friendly Tool for Finding-Based Diagnostic Report and Image Retrieval; RSNA 1996. From Radiographics 1996. pp. 923-933.

* cited by examiner

SYSTEM AND METHOD FOR STORING A CANDIDATE REPORT

FIELD OF THE INVENTION

The invention relates the field of medical reports, and in particular to a system and method for storing a candidate report.

BACKGROUND OF THE INVENTION

Diagnostic reports generated as a result of medical procedure contain a wealth of information, comprising diagnostic imaging results, clinical history and annotations by healthcare professionals.

Radiologists typically process up to thirty cases per hour. When facing a challenging case, radiologists turn to information sources to complete the diagnosis. These information sources may include scientific publications, but most frequently include previous cases. For this reason, exemplary and interesting cases are collected in databases by the radiologists themselves. Such databases may take many forms: local folders on a computer system, accessible to individual users or to multiple users, PACS systems, a reference case manager like mypacs.net (www.mypacs.net).

These databases comprise many reports, by far exceeding the number of cases that any single person can recall. Even a personal folder, populated by one healthcare professional such as a radiologist, will typically grow beyond the point where its user can recall its full content. The problem is compounded by the access to databases of multiple users. For example, over 1 million diagnostic reports were generated in 1991-1996 by the Department of Radiology alone, and stored in the radiology information system (RIS) of the University of Texas Medical Branch. The ability to search the databases and retrieve relevant matches therefore becomes increasingly important. As medical imaging becomes more affordable, and the diversity of diagnostic modalities and therapeutic treatments increase, the amount of data being stored increases, and the problem becomes even more critical.

SUMMARY OF THE INVENTION

It is an object of the invention to provide a system and method for storing a candidate report.

The invention is defined by the independent claims. Advantageous embodiments are defined in the dependent claims.

According to a first aspect of the invention, a system is provided for storing a candidate report, comprising:
 a report database configured to store and provide reports;
 a user input configured to provide the candidate report;
 a query database configured to store and provide queries, wherein the queries are suitable for searching in the report database;
 a searcher configured to:
 retrieve one or more queries from the query database;
 retrieve the candidate report from the user input;
 execute the one or more queries on the candidate report to determine the relevance of the candidate report, and
 store the candidate report in the report database if the relevance exceeds a predetermined value.

The invention is based upon the insight that the retrievability of reports by the healthcare professional may be made more efficient by reducing the proportion of low-quality reports in the database. A further insight is that it may be even more efficient to evaluate a report for inclusion in the database before it is included.

In some cases, this may also reduce the number of reports in the database. This is completely opposite to the conventional approach, which strives to improve the retrievability of reports by more complex search algorithms to search through all reports.

The invention provides a check, prior to storing, to evaluate whether the candidate diagnostic report would actually be a worthwhile addition to the database. If not, it is by default not added. The healthcare professional is alerted when reporting on a case, so that superfluous cases are identified and left out of the database. In this way, the quality of the database reports is maintained, so that future retrievals by the same user or different users, are more efficient and accurate.

The check is performed by using a database of previous queries, selecting one or more queries, and executing the queries on the candidate report. Based upon the results, the relevance of the candidate report is determined. This relevance is compared to a predetermined value, which represents a threshold for inclusion in the database. If the candidate report exceeds this value, the system adds the candidate report to the report database. In other words, the system determines whether the candidate report would have been retrieved from the report database if it had been part of the database when the one or more queries were performed.

An additional advantage is a saving in time for the healthcare professional. In many cases, the healthcare professional must spend extra time to prepare a report for storage and to increase the chances of future retrieval. However, the professional's time is limited and writing a basic report takes considerably less time than writing a full reference report. This has been estimated to be approximately a 20%/80% relationship between writing a basic report and writing a full report. The efficiency is improved by directing the professional to spend the most time on worthwhile reports, and less time on less-worthwhile reports.

A further advantage is the incentive to spend the extra time on the report if the invention indicates prior to storage that the report appears worthwhile to the rest of the healthcare community. The contribution of reports, and the appreciation for the reports expressed by the invention, provides immediate feedback to the professional about his/her performance, and provides a source of motivation.

The difference between a full report and a basic report depends on the type of report. For example, a radiologist wishing to create a reference report may add supplementary information, such as differential diagnoses or references to publications. The radiologist may also improve the chances of retrieval based upon knowledge of the retrieval search engine algorithm, such as adding a selection of appropriate keywords, classifications, standardizing language, standardized layout with standardized headings.

In another aspect of the invention, the searcher may be further configured to select the one or more queries for retrieval from the query database, based upon a parameter selected from the group consisting of: queries relating to a specific imaging modality, queries performed by a specific individual, queries performed by a specific group of individuals, queries performed by a specific healthcare specialism, queries performed from a specific location, queries performed over specific periods of time, queries which produced no matches when last performed, a specific number of queries, queries relating to a specific anatomical feature, queries with a specific classification, and any combination thereof.

To reduce the required computational power or to increase efficiency, the queries used to check the report prior to possible storage may be limited based upon context of the query, such as only those queries performed by the radiological department, or a healthcare professional may only be interested in his/her own queries. Other possibilities which may be advantageous are the queries of the last few months or the last so-many queries performed.

It may be particularly advantageous to use queries which previously produced no matches—if the candidate report matched to a high-enough degree, this would indicate that the report is an extremely valuable addition.

Of course, in practice, the healthcare professional may use a combination of these in an iterative fashion. The skilled person will also realize that such parameters may be performed successively, and that a composite relevance or importance factor may be derived from these multiple determinations.

In a further aspect of the invention, the searcher is configured to determine the relevance of a report, based upon a parameter selected from: the degree of the match between the one or more queries and the report, the number of queries producing a match, the number of unique queries producing a match, or any combination thereof.

Methods of the determination of relevance are well-known in the art, so the invention is not limited to any particular definition. As the relevance of the candidate document is determined to accommodate future retrievals, it may be advantageous to determine the relevance of the candidate report in a comparable way to the relevance determination made when the queries were originally executed by users attempting to retrieve reports from the report database.

In another aspect of the invention, the system further comprises a display configured to provide a representation to the user of the relevance of the candidate report.

In this way, the user who has a report available receives direct feedback about its value to the database.

According to a further aspect of the invention, the searcher is further configured to:

retrieve a multiplicity of reports from the report database;

execute the one or more queries on the multiplicity of reports to determine a match list for each query, wherein the match list comprises the relevance values of the members of the match list;

determine the predetermined value, based upon relevance values of the match list.

It may be advantageous to create match lists for queries. By executing the query for a large number of reports in the database, a match list of reports with the most relevant relevance values may be compiled for each query. The relevance values in the match list then form the basis for determining the threshold for including the candidate report in the database.

The members of the match list may be determined in any appropriate way known in the art, such as by selecting the relevance values of reports exceeding a second predetermined value, or by selecting a predetermined number of the highest relevance values of reports.

The searcher may then be further configured to store the match list in the query database associated with the corresponding query, and retrieve the match list associated with the one or more queries from the query database.

It may be advantageous to compile the match lists prior to providing the candidate report, so that the computational power required is reduced. This compilation may also be performed at regular intervals. The match lists may be stored in any location, but it may be most convenient to store them in the query database.

As an example, the predetermined value of the threshold for storing the candidate report may be determined by ranking the match list, based upon the relevance of the members of the match list, and determining the predetermined value based upon a position in the ranked match list.

Determining the relevance of the candidate report may then be simplified by comparing its relevance to a fictitious position in the ranked list. If the candidate report would have been higher than a predetermined position in the ranked list, the candidate report is considered valuable enough to be placed in the report database. This simplifies the consideration of the relevance of the candidate report.

The searcher may also be configured to store the predetermined value in the query database associated with the corresponding query, and retrieve the predetermined value associated with the one or more queries from the query database.

This may be implemented by providing or determining a threshold value for each query. This may be advantageous because it requires a low level of processing power when determining whether to store the candidate report or not.

The match list may further comprise a report identification of the members of the match list. This may be advantageous as it may be used by the user to locate reports which are considered more relevant than the candidate report. This may be useful if the user requires more feedback about why the candidate report is not ranked higher. Similarly, the user may wish to locate reports considered less relevant than the candidate report.

It may be advantageous to include a display in the system, configured to provide a representation to the user of the relevance of the candidate report. The user is then informed about how worthwhile the candidate report is considered to be.

This may also be advantageous when the user wishes to add annotations or make other changes to increase the relevance. It is also envisioned that a dynamic relevance be provided so that as changes are made, the relevance is displayed immediately providing an efficient method for the professional to optimize the future chance of retrieval.

In a still further aspect of the invention, the user input is further configured to provide a request by the user to store the candidate report in the report database, and the searcher is further configured to store the candidate report in the report database in response to the user request.

It is envisioned that the system is provided with a predetermined threshold for relevance, so that once the user provides the report to the system, it is automatically stored if the relevance exceeds the predetermined threshold. However, it may be advantageous to always give storage confirmation to the user, or to provide the user with means to determine that the report is always stored, irrespective of the relevance. This may be useful when reports in a new area or new discipline are being created for which there are no earlier queries.

The system of the invention in any of its embodiments may be comprised in a workstation or a medical imaging acquisition apparatus.

In another aspect of the invention, a method is provided for storing a candidate report, the method comprising:

providing a report database;

providing the candidate report;

providing a query database, wherein the queries are suitable for searching in the report database;

retrieving one or more queries from the query database;

executing the one or more queries on the candidate report to determine the relevance of the candidate report, and storing the candidate report in the report database if the relevance exceeds a predetermined value.

The method may further comprise:

retrieving a multiplicity of reports from the report database;

executing the one or more queries on the multiplicity of reports to determine a match list for each query, wherein the match list comprises the relevance values of the members of the match list; and determining the predetermined value based upon relevance values of the match list.

A computer program product is also envisioned for carrying out the method of the invention, when loaded and run on a computer.

It will be appreciated by those skilled in the art that two or more of the above-mentioned embodiments, implementations, and/or aspects of the invention may be combined in any way deemed useful.

Modifications and variations of the image acquisition apparatus, of the workstation, of the system, and/or of the computer program product, which correspond to the described modifications and variations of the method, can be carried out by a person skilled in the art on the basis of the present description.

It will also be obvious to the skilled person that the invention does not need to be limited to reports generated by radiologists. It may be used with reports comprising any kind of medical data, although it may be advantageous for reports comprising medical imaging data. These may require considerable storage capacity, and reducing the number of reports stored may also reduce equipments costs.

This imaging data may be acquired by any imaging modality, such as X-ray Imaging, Computed Tomography (CT), Magnetic Resonance Imaging (MRI), Ultrasound (US), Positron Emission Tomography (PET), Single Photon Emission Computed Tomography (SPECT) and Nuclear Medicine (NM).

It is also envisioned that the invention may be used for any information content to be accessed by a database, such as web pages being compiled for addition to the Internet. Search engines are known in the art for searching the Internet, and producing results to a query based upon relevance. In that case, the candidate report may be considered to be the web page as it is being created and the Internet is the report database. It is known that some Internet search engines maintain a database of queries, but the queries are not used to indicate the importance of the web page prior to uploading to the Internet.

BRIEF DESCRIPTION OF THE DRAWINGS

These and other aspects of the invention are apparent from and will be elucidated with reference to the embodiments described hereinafter.

In the drawings.

The Figures are purely diagrammatic and not drawn to scale. Particularly for clarity, some dimensions are exaggerated strongly. Similar components in the Figures are denoted by the same reference numerals as much as possible.

DETAILED DESCRIPTION OF THE PREFERRED EMBODIMENTS

Figure 1:
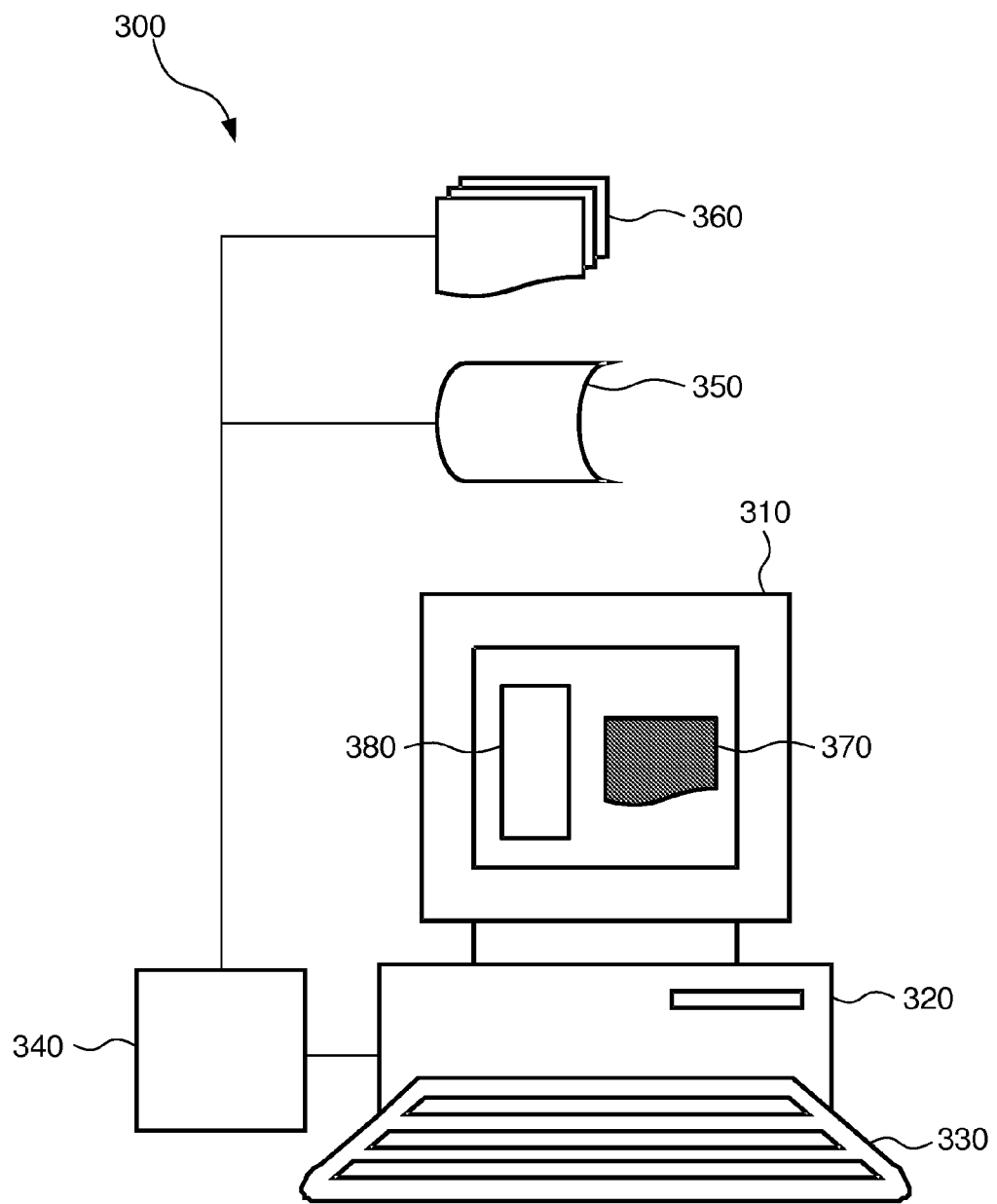
FIG. 1 shows the system according to the invention.

A system 300 for storing a candidate report 370 is depicted in FIG. 1. The system 300 comprises:

a report database 360 configured to store and provide reports. These may be local folders comprised in the system 300, accessible to individual users or to multiple users. The report database may also be an on-line system, such as a PACS system or a reference case manager like mypacs.net, which may be made available by providing the system 300 with an appropriate network connection. The database may typically also allow deletion of and annotations to the reports stored;

a user input 330 configured to provide the candidate report 370. Typically, the user input 330 provides for interaction with the system in any form known in the art. For example, as icons, thumbnails, menus, and pull-down menus. The user input 330 may also comprise a keyboard, mouse, trackball, pointer, drawing tablet or the like. The user input 330 may also provide speech recognition capabilities. As the user input 330 provides a candidate report 370, typically the user input 330 will cooperate with a processor 320 to provide the report handling functions, such as editing and word-processing facilities;

a query database 350 configured to store and provide queries, wherein the queries are suitable for searching in the report database 360. It may be convenient to locate the query database 350 with the report database 360, as the queries are associated with the reports, and are compiled from queries to the report database 360. However, any location is envisioned, such as locally or on-line via an appropriate network connection;

a searcher 340 configured to:

retrieve one or more queries from the query database 350;

retrieve the candidate report from the user input 330;

execute the one or more queries on the candidate report 370 to determine the relevance of the candidate report 370, and store the candidate report 370 in the report database 360 if the relevance exceeds a predetermined value.

The searcher 340 may be implemented in any appropriate way known to the skilled person, such as a processor provided with connections to the databases 350, 360.

The queries in the query database 350 are suitable for searching in the report database 360. The nature of the queries may be of any appropriate type known to the person skilled in the art, and depends upon the nature of the reports and the type of users. The query also depends upon the way in which the searcher 340 is configured to execute the query to determine the relevance of the candidate report 370.

For example, the article "MoSearch: A radiologist-friendly tool for finding-based diagnostic report and image retrieval", by Ramaswamy, Patterson, Yin, Goodacre (RSNA 1996); Radiographics 1996, 16, pages 923-933, discloses a software package that allows radiologists to conduct sophisticated real-time searches of diagnostic reports on the basis of patient characteristics, modality used, anatomy examined, and imaging findings and to easily review, refine, and output the results. It was designed and implemented in a large academic hospital. A notable feature of this system of the prior art is the use of synonym-matching and syntactic cues, which allows it to identify findings within the text of a diagnostic report much more accurately than a simple keyword search can. This type of system can be easily and inexpensively implemented on a personal-computer.

Described in this article are also other techniques known to the skilled person, such as coding the reports, structured report entry according to a prescribed format, natural language processing of the text in the reports, simple or complex keyword searches.

The skilled person will also be familiar with other search algorithms used by Internet search engines to determine relevance, such as www.google.com and www.yahoo.com, where the relevance is translated to a ranked list of hits.

It may therefore be advantageous for the skilled person implementing the invention to define the queries, the reports together with the algorithm for determining relevance, so that the requirements of the users of the system may be taken into account.

Figure 3:
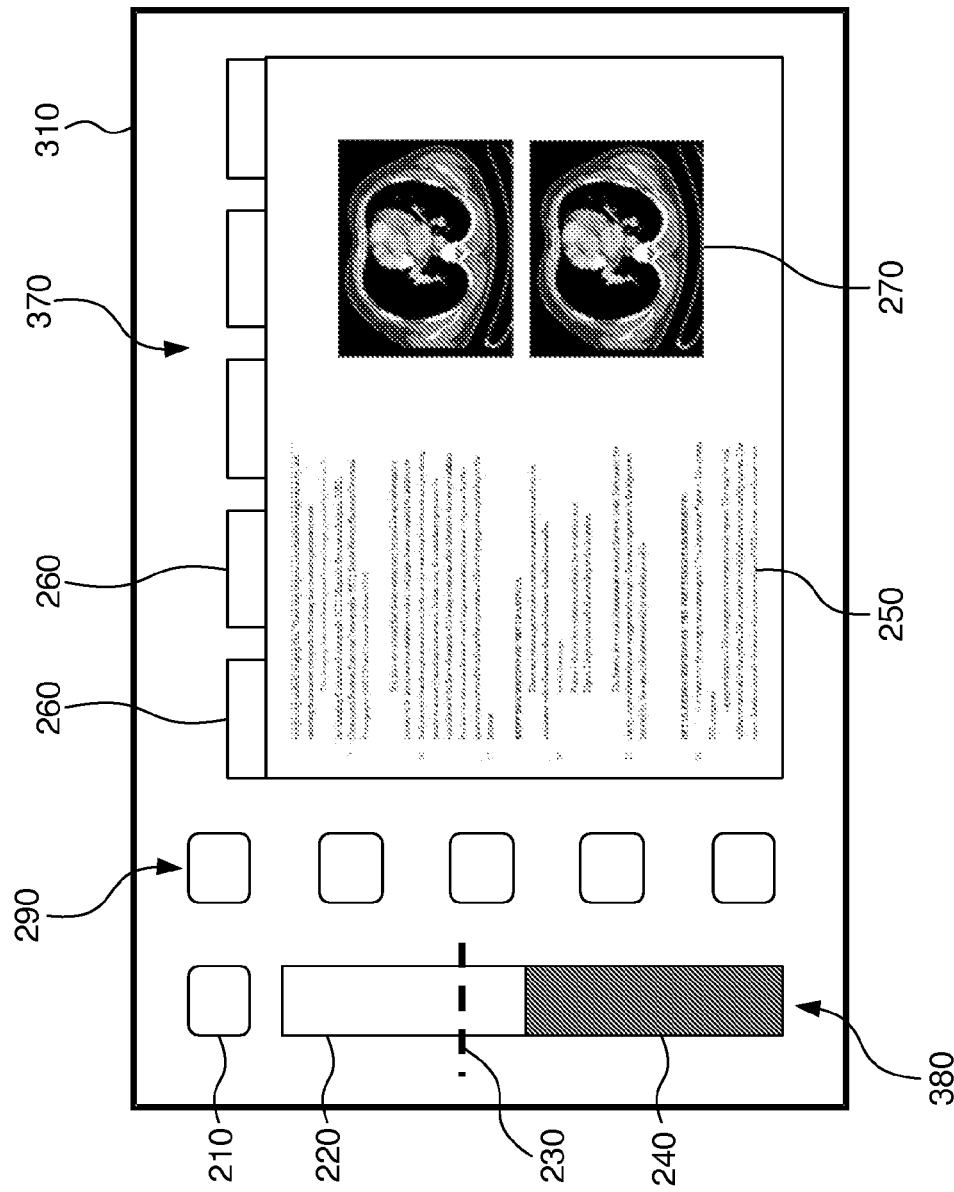
FIG. 3 depicts a possible representation to the user on a display.

FIG. 3 depicts a possible implementation of the representations which may be provided to the user on a display 310, which may be comprised in the system 300. The display comprises a representation of the candidate report 370 and a representation of the relevance 380 of said candidate report.

Many such representations are possible. For example, the candidate report 370 may be made available as a series of tabs 260 for navigation. Such tabs 260 may include History, Findings, DDx, Diagnosis, Discussion, References and Comments. Generally, such a report may comprise imaging results 270 and some explanatory text 250. It may be advantageous for the processor 320 to be configured so as to provide word processing facilities, so that the explanatory text 250 may be edited.

The representation of the relevance 380 may take any form known in the art. For example, the skilled person will be aware of relevance results expressed as a percentage, conventionally 0 to 100%. FIG. 3 gives a more schematic representation 380, comprising a level indicator 240 inside a box 220. The level indicator 240 is a shaded bar representing the values between 0 and the percentage relevance of the candidate report 370. This shaded bar 240 is overlaid onto the unshaded box 220 representing the relevance levels 0 to 100%.

Optionally, a control 210 may be provided for the user to request a determination of the relevance of the candidate report 370. It is also envisioned that such a control is integrated into a word-processing package, so that when a candidate report 370 is saved in a buffer folder, the relevance is automatically calculated and displayed 380.

Optionally, other controls 290 may be available to provide other convenient functions to the user, such as allowing the user to specify further details for the method, or to overrule determinations of the system.

Figure 2:
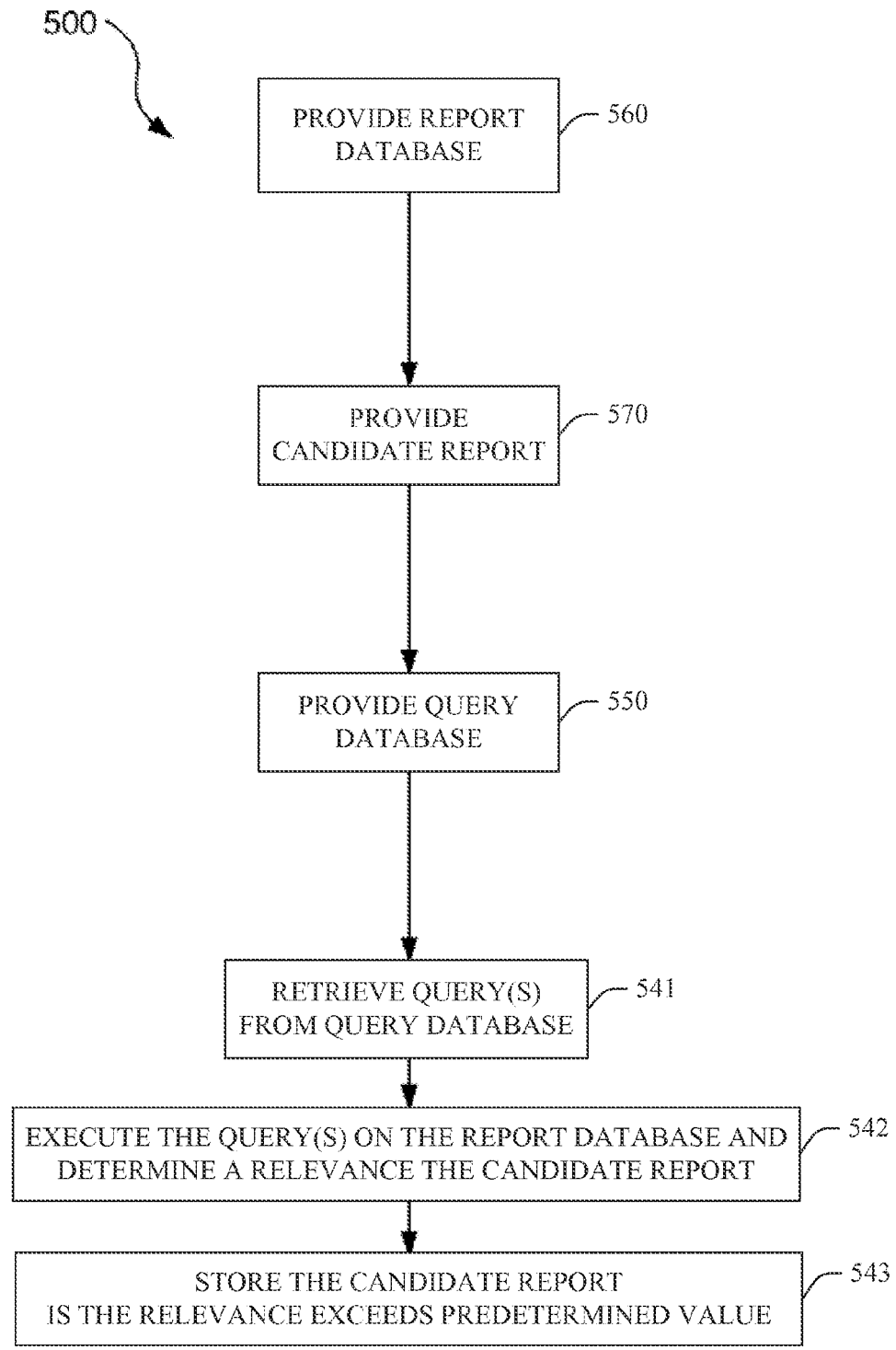
FIG. 2 depicts the method according to the invention.

The system is configured for performing the method 500 according to the invention, which is depicted in FIG. 2. The method comprises:

providing 560 a report database 360;
providing 570 the candidate report 370;
providing 550 a query database 350, wherein the queries are suitable for searching in the report database 360;
retrieving 541 one or more queries from the query database 350;
executing 542 the one or more queries on the candidate report 370 to determine the relevance of the candidate report 370, and
storing 543 the candidate report 370 in the report database 360 if the relevance exceeds a predetermined value.

During use of the system, the candidate report 370 is provided 570 by the user input 330.

One or more queries are retrieved 541 from the query database 350. The number of queries retrieved 541 may be anywhere between one and the entire contents of the query database. The selection of the queries to be retrieved may be determined by the skilled person, based upon the requirements of the user and the computational power available. For example, the queries retrieved may be those relating to:

a specific imaging modality only, such as reports comprising MRI results. In practice, a professional may wish to evaluate images made with more than one modality, for example a radiologist may wish to look at X-ray images as well as MRI and CT scans; therefore, queries relating to one or more specific modalities may be retrieved;

queries performed by a specific individual, such as the user himself or a recognized expert in the field;

queries performed by a specific group of individuals, such as the trainees in the radiology department;

queries performed by a specific healthcare specialism, such as all radiologists;

queries performed from a specific location, such as a particular hospital or a particular department;

queries performed over a specific period of time, for example in the last 3 months;

queries which produced no matches when last performed, because a candidate report which scored a high-relevance for such a query would be a particularly valuable addition to the database;

a specific number of queries, such as the last 1000 queries or the most popular 1000 queries;

queries relating to a specific anatomical feature, such as brain-head, neck-spine;

queries with a specific classification, such as prototypical, borderline, difficult.

It will be apparent to the skilled person that these may be used in combination, or in succession, or even as part of an iterative evaluation. Such an algorithm may be provided automatically, or the user may be allowed to indicate via the user input 330 personal selections of queries.

The queries retrieved 541 are then executed 542 on the candidate report 370 to determine its relevance. The relevance 380 is typically then displayed on the display 310.

For example, the relevance may be determined 542 based upon the degree of the match between the queries retrieved and the report, the number of queries producing a match, the number of unique queries producing a match, or any combination thereof. Typically, an appropriate algorithm for determining relevance will be selected by the skilled person, and this algorithm will be used when queries are executed to retrieve reports from the database 360. It may be advantageous to use the same algorithm to determine the relevance of the candidate report 370, although this is not essential. The skilled person will be able to tune the algorithms to achieve the desired efficiency of operation.

In a fully automatic system, the relevance of the candidate report 370 is compared by the searcher 340 to a predetermined value, and if the relevance exceeds this value, the searcher 340 stores 543 the candidate report 370 in the report database 360.

The predetermined value may also be represented on the display, for example as a line 230 at an appropriate position in the unshaded box 220. This provides a simple feedback to the user of the relative relevance as being the difference between the extent of the shaded bar 240 and the required relevance 230 for inclusion.

A highly-automated system is also envisioned, in which the relevance of the candidate report 370 is represented 380 on the display 310, but storage is not automatic. A control 290 is provided so that the user requests the searcher 340 to store the candidate. This may be advantageous in those cases where:

the user wishes to add the candidate report 370 to the database 360 without considering the determined relevance. For example, if a user wishes to anticipate future queries, or if the candidate report 370 is related to a new field or discipline for which no queries would be present in the query database 350;

the user wishes to be provided with a dynamic representation 380 of the relevance of the candidate report 370. In this way, the user may edit the candidate report 370 by adding content to increase the relevance, such as annotations, keywords, references, links. This would be most efficient when the user is provided with some understanding of the way in which the relevance algorithm determines the relevance. Determination 542 of the relevance may be automatic, or may be requested by the user using the control 210 provided; or the user wishes to be provided with a dynamic representation 380 of the relevance of the candidate report 370. If the relevance is high enough, the user may edit the candidate report 370 by adding content to enrich the contents and to make it more useful to other users of the system. Examples of content that may be added include: an appropriate title, relevant facts from the patient's history, an overview of findings, differential diagnoses (DDx), the eventual diagnosis, discussion, references and links to publications, links to other relevant reports. Determination 542 of the relevance may be automatic, or may be requested by the user using the control 210 provided. This provides an incentive to the user to invest the extra effort into increasing the quality of the report for future retrieval by other users.

A further control 290 may be provided enabling the user to request the searcher 340 not to store the candidate report, irrespective of the determined relevance. This may be advantageous in those cases where the user wishes to postpone the work on the report, or simply to exit the method.

The predetermined value which represents the threshold for inclusion in the report database may be a single value for all candidate reports 370. However, it may be advantageous for the skilled person to be able to optimize the system by providing different predetermined values which the searcher 340 may utilize under different circumstances.

For example, the predetermined value may be related to a specific imaging modality, a specific individual, a specific group of individuals, a specific healthcare specialism, a specific location, a specific anatomical feature, a specific classification, or any combination thereof. It is also envisioned that the predetermined value may be dynamic to allow the skilled person to control the flow of reports in the database—for example, it may be advantageous to set the threshold relatively low when a new database 360 is created to quickly grow the database 360, and then raise the threshold as the database 360 becomes full.

The predetermined value may also be determined based upon the current contents of the report database 360. The searcher 340 may be further configured to retrieve a multiplicity of reports from the report database and to execute the retrieved queries on these reports to determine a list of matches for each query. In other words, the searcher 340 executes each of the retrieved queries on the report database 360 to see what the hits are. This list of matches may have no members if no hits are obtained, or it may include all reports in the report database 360 if the query is very generic. Typically, the number of members will be somewhere between these extremes, and may be limited in any appropriate way, such as only the relevance values exceeding a second predetermined value, or a predetermined number of the highest relevance values such as the top ten.

The match list comprises the relevance values of the hits. These relevance values may then be used to determine the predetermined value in any appropriate way known to the skilled person. For example, the minimum relevance, the maximum relevance, a statistical operation such as average relevance, or a weighted average.

The determination of a matched list for each of the retrieved queries may be performed immediately prior to determining the relevance of the candidate report 370. This may be computationally intensive, and therefore it may be advantageous to determine the matched list for each query at an earlier time.

For example, the match lists may be determined during off-peak times, and the predetermined values stored at some convenient location, such as in the query database 350. The searcher 340 must then be further configured to store and retrieve the predetermined value for each of the retrieved queries.

It is also envisioned that the match list for each query is stored. This may be advantageous in those cases where the threshold for storage is determined by a statistical operation in which the match list including the candidate report is compared to the match list without the report, or where the match list is ranked and the relevance is indicated as a potential position in this ranked list. For example, if for each query the top-ten most relevant hits are stored, then the threshold for storing the candidate report is that the report would be positioned in the top-five if added to the database 360.

Alternatively, in those cases where the user is permitted to request storage of the candidate report 370, the match list may be represented on the display 310 with an indication of where the candidate report 370 would appear in a ranked list. This is a particularly intuitive representation, allowing the user to request storage where appropriate.

It may be further advantageous to provide the user with further controls 290 to influence the future retrieval of the candidate report 370, such as:

a copy relevance control 290 to copy keywords or annotations from a report corresponding to a relevance in the match list higher than the relevance of the candidate report 370. For example, if the user wishes to ensure that the report is always retrieved in response to a query, the match list may also comprise identifications of the reports corresponding to the relevance values. The searcher 340 is then configured to store and retrieve these report identifications comprised in the match list, and the display 310 is configured to display the list to the user. By selecting the copy relevance control 290 and an entry in the list, the searcher copies the appropriate keywords and annotations from this entry in the list to the candidate report 370, giving the candidate report 370 at least the same relevance value. Alternatively, the same control may be used to reduce the relevance of the candidate report 370 for one or more queries;

a retrieval alert control 290 so that the user is alerted when the candidate report 370 is retrieved by another user from the database 360 after it has been added to the database 360. This also provides an extra incentive to the user as he/she receives feedback that the report is actually being retrieved by future queries;

a report retrieval control 290 so that the user may select a report already present in the database 360, and retrieve it so that it becomes a new candidate report 370. This allows a user to improve existing reports to increase their relevance, or to retrieve older candidate reports 370 which were stored and to review the change in relevance experienced over a period of time; and a query alert control 290 so that the user may request the system to monitor one or more queries. The searcher 340 may be configured to monitor the match lists for the selected queries, and to send an alert to the user if a new hit is added to the list. This may be particularly advantageous for queries which return no hits at a particular moment in time. The skilled person will recognize this concept from the Google Alert service.

The skilled person, provided with the details of the method disclosed, will be able to implement numerous systems for performing the method, in addition to the systems disclosed in this application. Typically, such a system will comprise a computer, and the skilled person will be able to assign the function to a combination of hardware and software, and consequently implement a computer program to carry out these methods when loaded and run on the computer.

A user may use a workstation to perform interactions, for example during the preparation of the medical report, the annotation of such a report and the confirmation that the report is to be stored. The workstation may then comprise a processor 320 to assist in performing the user interactions and in performing the method of the invention. The workstation may then comprise the system according to the invention. It is also envisioned that the system 300 may be comprised in a medical image acquisition apparatus.

It will be apparent to the skilled person that a plurality of the functions of the system may be implemented in parallel, so that the same hardware may be utilized to provide a number of report databases. For example, it may be advantageous to limit a particular report database to one particular discipline, such as radiology. This allows the skilled person to optimize the query definition, the report structure and the relevance algorithm for radiologists. A second database for a second discipline, such as pathology, may be provided in parallel, so that the second query definition, the second report structure and the second relevance algorithm may then be optimized for pathologists.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer.

In the system claim enumerating a user input, a searcher, a report database, a query database, and a display, several of these means may be embodied by one and the same item of hardware.

The mere fact that certain measures are recited in mutually different dependent claims does not indicate that a combination of these measures cannot be used to advantage.

The invention claimed is:

1. A system for storing a candidate report, the system comprising:
a report database configured to store and provide reports;
a user input, of a computer, configured to create and edit the candidate report, wherein the candidate report is not stored in the report database;
a query database configured to store and provide queries, wherein the queries are suitable for searching in the report database;
a hardware searcher configured to:
retrieve one or more queries from the query database;
retrieve the candidate report from the user input;
execute the one or more queries on the candidate report to determine the relevance of the candidate report;
infer from the relevance that the candidate report would not have been retrieved had the candidate report been part of the report database and the one or more one or more queries been executed on the report database including the candidate report;
check the report through the relevance to determine whether the candidate report is a worthwhile addition to the report database, and
store the candidate report in the report database only if the relevance exceeds a predetermined value.

2. The system of claim 1, wherein:
the searcher is further configured to:
retrieve a multiplicity of reports from the report database;
execute the one or more queries on the multiplicity of reports to determine a match list for each query, wherein the match list comprises the relevance values of the members of the match list;
determine the predetermined value, based upon relevance values of the members of the match list.

3. The system of claim 2, wherein:
the searcher is further configured to:
store the predetermined value in the query database associated with the corresponding query, and
retrieve the predetermined value associated with the one or more queries from the query database.

4. The system of claim 2, wherein:
the searcher is further configured to:
store the match list in the query database associated with the corresponding query, and
retrieve the match list associated with the one or more queries from the query database.

5. The system of claim 4, wherein the match list further comprises:
a report identification of the members of the match list.

6. The system of claim 2, wherein:
the predetermined value is determined by:
ranking the match list, based upon the relevance of the members of the match list, and
determining the predetermined value, based upon a position in the ranked match list.

7. The system of claim 2, wherein the members of the match list are determined by selecting reports with relevance values exceeding a second predetermined value, or by selecting a predetermined number of reports with the highest relevance values.

8. The system of claim 1, wherein:
the searcher is configured to determine the relevance of a report, based upon a parameter selected from:
the degree of the match between the one or more queries and the report, the number of queries producing a match, the number of unique queries producing a match, or any combination thereof.

9. The system of claim 1, wherein the system further comprises:
a display configured to provide a representation to the user of the relevance of the candidate report.

10. The system of claim 1, wherein:
the user input is further configured to provide a request by the user to store the candidate report in the report database, and
the searcher is further configured to store the candidate report in the report database in response to the user request.

11. The system of claim 1, wherein:
the searcher is further configured to select the one or more queries for retrieval from the query database, based upon a parameter selected from the group consisting of:
queries relating to a specific imaging modality, queries performed by a specific individual, queries performed by a specific group of individuals, queries performed by a specific healthcare specialism, queries performed from a specific location, queries performed over a specific period of time, queries which produced no matches when last performed, specific number of queries, queries relating to a specific anatomical feature, queries with a specific classification, and any combination thereof.

12. A computer comprising the system according to claim 1.

13. A method of storing a candidate report, the method comprising:
provide a report database;
providing the candidate report, wherein the candidate report is a text based structured report with natural language text and the candidate report is not in the report database;
providing a query database, wherein the queries are suitable for searching in the report database;
retrieving one or more queries from the query database;
executing, via a computer processor, the one or more queries on the candidate report to determine the relevance of the candidate report;
inferring from the relevance that the candidate report would not have been retrieved had the candidate report been part of the report database and the one or more one or more queries been executed on the report database including the candidate report; and
checking the report through the relevance to determine whether the candidate report is a worthwhile addition to the report database, and
storing the candidate report in the report database only if the relevance exceeds a predetermined value.

14. The method of claim 13, wherein the method further comprises:
retrieving a multiplicity of reports from the report database;
executing the one or more queries on the multiplicity of reports to determine a match list for each query, wherein the match list comprises the relevance values of the members of the match list; and
determining the predetermined value, based upon relevance values of the members of the match list.

15. The method of claim 13, further comprising:
editing the candidate report in response to the relevance failing to exceed the predetermined value by adding text to the candidate report, creating an updated candidate report, and further comprising:
executing the one or more queries on the updated candidate report to determine the relevance of the updated candidate report, and
storing the updated candidate report in the report database if the relevance exceeds the predetermined value.

16. The method of claim 15, further comprising:
identifying text that increases a relevance of the candidate report to the one or more queries; and
adding the identified text to the candidate report to create the updated candidate report.

17. The method of claim 15, further comprising:
determining the added text based on prior knowledge of a search retrieval algorithm used to execute the one or more queries.

18. A memory device encoded with a computer program product for carrying out the method of claim 13, when loaded and run on a computer.

19. A method of storing a candidate report, the method comprising:
providing a report database;
providing the candidate report, wherein the candidate report is a text based structured report with natural language text and the candidate report is not in the report database;
providing a query database, wherein the queries are suitable for searching in the report database;
retrieving one or more queries from the query database;
executing, via a computer processor, the one or more queries on the candidate report to determine the relevance of the candidate report;
storing the candidate report in the report database only if the relevance exceeds a predetermined value;
identifying, based on prior knowledge of a search retrieval algorithm used to execute the one or more queries, text that increases a relevance of the candidate report to the one or more queries;
editing the candidate report in response to the relevance failing to exceed the predetermined value by adding the identified text to the candidate report, creating an updated candidate report;
executing the one or more queries on the updated candidate report to determine the relevance of the updated candidate report; and
storing the updated candidate report in the report database if the relevance exceeds the predetermined value.

* * * * *